(12) United States Patent
Schulze

(10) Patent No.: US 6,918,871 B2
(45) Date of Patent: Jul. 19, 2005

(54) METHOD FOR ACCESSING CAVITY

(75) Inventor: Dale R. Schulze, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/465,098

(22) Filed: Jun. 19, 2003

(65) Prior Publication Data

US 2004/0260147 A1 Dec. 23, 2004

(51) Int. Cl.[7] .............................................. A61B 1/04
(52) U.S. Cl. ...................................... 600/114; 128/898
(58) Field of Search ................................ 600/114, 121, 600/153; 128/898

(56) References Cited

U.S. PATENT DOCUMENTS

| | | | |
|---|---|---|---|
| 5,078,743 A | | 1/1992 | Mikalov et al. |
| 5,112,310 A | * | 5/1992 | Grobe ......................... 604/175 |
| 5,167,627 A | | 12/1992 | Clegg et al. |
| 5,356,391 A | | 10/1994 | Stewart |
| 5,813,976 A | * | 9/1998 | Filipi et al. ................. 600/102 |
| 5,851,195 A | * | 12/1998 | Gill ............................. 604/500 |
| 6,535,764 B2 | * | 3/2003 | Imran et al. .................. 607/40 |

FOREIGN PATENT DOCUMENTS

| | | |
|---|---|---|
| WO | WO 96/24296 A1 | 8/1996 |
| WO | WO 01/74260 A1 | 10/2001 |

OTHER PUBLICATIONS

DiMarino, Anthony J. Jr, MD, and Benjamin, Stanley B., MD; *Gastrointestinal Disease: An Endoscopic Approach*; published by Slack Incorporated, Thorofare, NJ, 2002, pp. 647–662.

* cited by examiner

Primary Examiner—Beverly M. Flanagan

(57) ABSTRACT

The present invention is a method for accessing the abdominal cavity of a patient in order to perform a medical procedure therein. The method can include the steps of introducing a medical device into the body cavity; providing a percutaneous incision to access the body cavity; and steering the medical device through the percutaneous incision. In one embodiment, a hollow steering element is advanced through the incision to guide a flexible endoscope postioned in the abdominal cavity.

14 Claims, 10 Drawing Sheets

METHOD FOR ACCESSING CAVITY

CROSS REFERENCE TO RELATED APPLICATION

This application cross references the following copending application filed on even date herewith: "Method for Endoscopic, Transgastric Access into the Abdominal Cavity", Ser. No. 10/465,061.

FIELD OF THE INVENTION

The present invention relates, in general, to the field of medicine, and more particularly, to flexible endoscopy of the gastrointestinal tract and to endoscopic surgery.

BACKGROUND

Laparoscopic surgery is one type of minimally invasive surgery in which a surgeon uses numerous trocar ports to access and visualize the tissue site of interest within the abdominal cavity of a fully anesthetized patient. The benefits of laparoscopic surgery, as compared to open incisional, abdominal surgery, include less pain, shorter recovery time, less scarring, and lower cost. Another way to access the abdominal cavity, however, is via natural openings (mouth, anus, vagina, urethra) of the body and through the peritoneal lining of the abdominal cavity. Obviously, the size and shape of instruments that may be passed through a bodily lumen in order to perform a medical procedure in the abdominal cavity are greatly restricted due to the anatomical properties of the lumen.

General surgeons, gastroenterologists, and other medical specialists routinely use flexible endoscopes for intraluminal (within the lumen of the alimentary canal) examination and treatment of the upper gastrointestinal (GI) tract, via the mouth, and the lower GI tract, via the anus. In these procedures, the physician pushes the flexible endoscope into the lumen, periodically pausing to articulate the distal end of the endoscope using external control knobs, to redirect the distal tip of the endoscope. In this way, the physician may navigate the crooked passageway of the upper GI past the pharynx, through the esophagus and gastro esophageal junction, and into the stomach. The physician must take great care not to injure the delicate mucosal lining of the lumen, which generally may stretch open to a diameter in the range of about 15–25 mm, but normally has a non-circular cross sectional configuration when relaxed.

One transluminal (passing through the lumen wall of the alimentary canal) procedure is placement of a PEG (percutaneous endoscopic gastrostomy) feeding tube in patients who are unable to ingest food orally. In a PEG procedure, a physician places the end of a specially adapted, flexible tube into the patient's stomach through a percutaneous incision in the patient's abdomen, using a flexible endoscope inserted orally and into the stomach to assist in the placement of the PEG tube. Methods have been developed, including Ponsky-Gauderer (Pull Through) technique, Sacks-Vine (Push Through) technique; Introducer technique, and Button technique. (See Chapter 38, pages 647–662 of "Gastrointestinal Disease, An Endoscopic Approach," edited by A. J. DiMarino, Jr., S. B. Benjamin, second edition, Slack Incorporated, Thorofare, N.J., 2002, incorporated herein by reference). Placement of a guide wire can include having the guide wire extend through the upper GI tract, with a first end of the wire extending out of the patient's mouth, and a second end of the wire extending out of the percutaneous incision in the abdomen. The first end of the guide wire is then attached to one end of the PEG tube. The physician next pulls the second end of the guide wire to pull the PEG tube through the esophagus and position the PEG tube so that its bulbous end abuts the inner gastric wall, and the rest of the PEG tube extends through the gastric and abdominal walls, and out of the abdomen. (There normally is not a space between the gastric and abdominal walls during this procedure, but it is possible to create a gap by physically lifting the abdominal wall away from the stomach or by insufflating the abdominal cavity with carbon dioxide gas, since this gap is actually part of the abdominal cavity.) While the PEG tube is in place, sometimes for several weeks, the gastric and abdominal walls heal together around the tube, essentially sealing the inside of the stomach from the abdominal cavity.

SUMMARY OF THE INVENTION

In one embodiment, the present invention provides a method for accessing a body cavity. The method can include the steps of introducing a medical device into the body cavity; providing a percutaneous incision to access the body cavity; and steering the medical device through the percutaneous incision.

The step of introducing the medical device into the body cavity can include introducing the medical device through a naturally occurring body orifice, such as with a flexible endoscope. In one embodiment, the medical device can be introduced through the mouth into the upper GI tract, and through a gastric opening in the stomach into the abdominal cavity. A steering device can be inserted through a percutaneous incision to guide the medical device in the abdominal cavity.

BRIEF DESCRIPTION OF THE DRAWINGS

The present invention may be best understood by referring to the detailed description and the following drawings.

DETAILED DESCRIPTION OF THE INVENTION

The present invention is a method for endoscopically accessing the abdominal cavity of a patient via the mouth and upper gastrointestinal tract. The transgastric approach of this method allows a physician to perform diagnostic or therapeutic procedures inside the abdominal cavity without creating a plurality of laparoscopic ports in the abdomen. Instead, the physician creates a single, percutaneous opening in the abdomen of the patient and at least one opening in the gastric wall.

Figure 1:
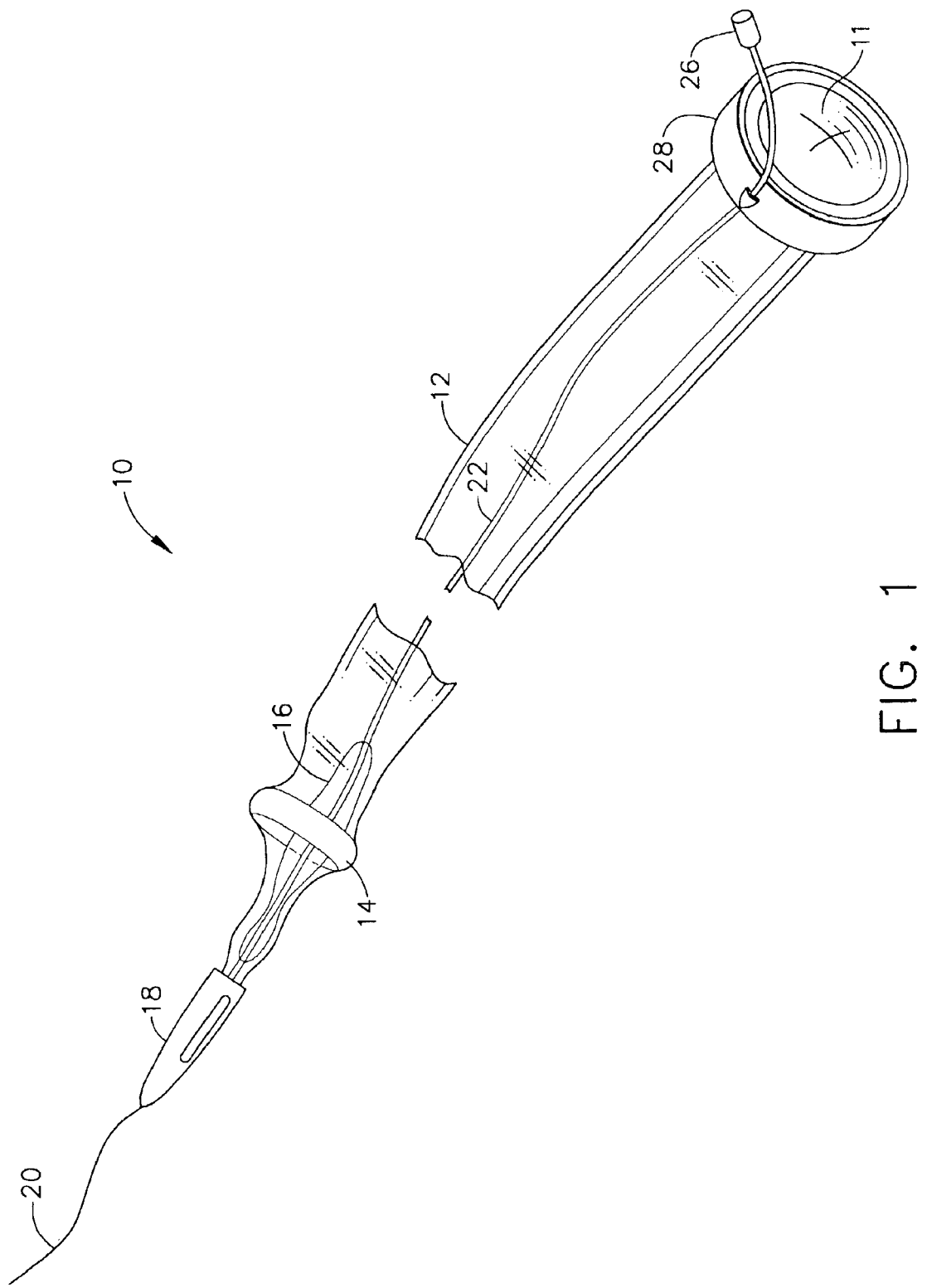
FIG. 1 illustrates an access device 10 adapted for receiving a flexible endoscope that is transorally positionable inside the upper gastrointestinal tract of a patient.

FIG. 1 illustrates an access device 10 adapted for receiving a flexible endoscope that is transorally positionable inside the upper gastrointestinal tract of a patient. Access device 10 comprises an elongate, flexible sheath 12 that has a lumen 13 of sufficient size to receive the endoscopic portion of at least one flexible, endoscopic instrument such as a flexible endoscope. (A standard gastroscope has a maximum shaft diameter of about 15 mm.) The length of sheath 12 is at least long enough to extend from outside the patient's mouth to inside the abdominal cavity to the area of interest. A preferable length for sheath 12 is approximately the same as the length of the endoscopic portion of a standard gastroscope, or at least about 165 centimeters.

The inner wall surface of sheath 12 is lubricious to facilitate insertion and removal of endoscopic instruments, preferably without the addition of medical lubricants. The outer wall surface of sheath 12 is adapted for ease of insertion into the upper GI tract without injuring the delicate mucosal lining. Sheath 12 is made of a material that is biocompatible, sterilizable using gamma radiation or other standard methods, and has a low permeability to irrigation and body fluids to maintain a relatively aseptic pathway through lumen 13. The material of sheath 12 is preferably inexpensive to allow disposal after use on one patient, and transparent for viewing portions of the upper gastrointestinal tract with the flexible endoscope. One example of a material suitable for sheath 12 is clear, low-density polyethylene tube having a wall thickness approximately in the range of 0.05 mm to 0.25 mm, and a diameter approximately in the range of 10 mm to 20 mm.

In other embodiments not shown, sheath 12 may be constructed with at least one longitudinal stiffening element attached to and extending along at least a portion of the length of sheath 12. The longitudinal stiffening element may be made of thin, flexible steel or plastic band to prevent kinking of sheath 12 as may occur, for example, at the gastro esophageal junction. Sheath 12 may also be constructed of two or more layers of the same or dissimilar materials in order to obtain the desired combination of properties listed above. For example, an inner layer may comprise an expanded PTFE tube or a polyester expandable sleeve and an outer layer may comprise a polyethylene tube.

The proximal portion of access device 10 remains extended from the patient's mouth during the medical procedure and comprises a cannula 28 attached to the proximal portion of sheath 12. A dilator tube 22 fluidly connects dilator 16 to a syringe fitting 26 that hangs freely from the proximal end of cannula 28 when not attached to a syringe. Cannula 28 is generally cylindrical in shape and may be made from a biocompatible plastic such as polyethylene. The operator may hold cannula 28 during insertion and removal of endoscopic instruments into access device 10.

Cannula 28 includes a proximal seal 11 for sealing around the shaft of the endoscopic instrument inserted into lumen 13. Proximal seal 11 is an elastomeric membrane with a small hole or slit in the center that easily stretches to the diameter of the endoscopic instrument. Proximal seal 11 helps prevent fluids that may enter channel 13 of access device 10 from spilling out of cannula 28. Proximal seal 11 also permits insufflation of the abdominal cavity with carbon dioxide gas, as is common in laparoscopic surgical procedures.

Figure 2:
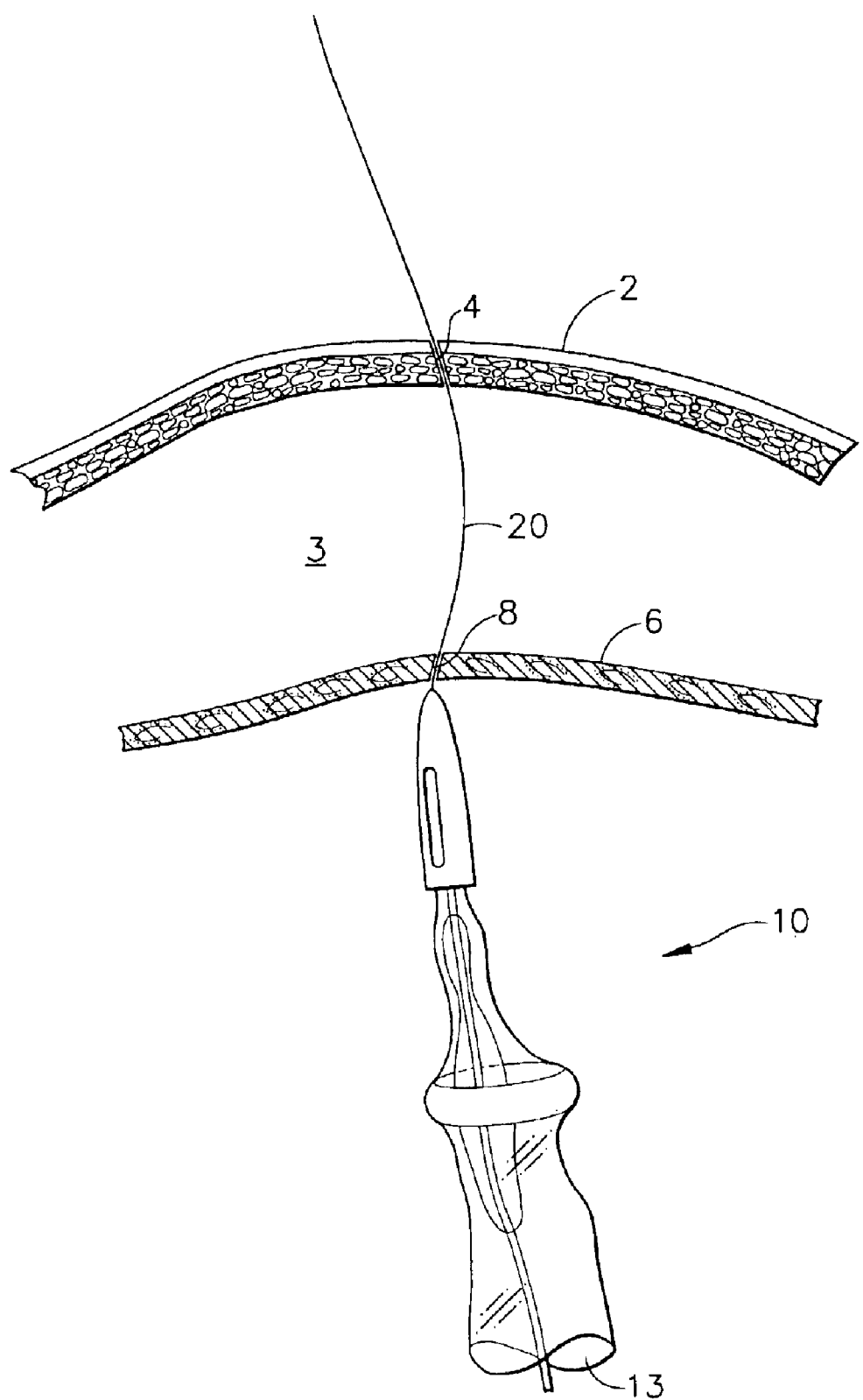
FIG. 2 illustrates the distal portion of access device 10 of FIG. 1 inside the stomach of the patient, and a tether 20 of access device 10 positioned through a gastric opening 8 of a gastric wall 6, an abdominal cavity 3, and an abdominal opening 4 of an abdominal wall 2.

Still referring to FIG. 1, the distal portion of access device 10 comprises an introducer tip 18, a locator 14, a tether 20, and a dilator 16. Tether 20 attaches to the distal end of sheath 12 and may be made from a polyester string, braided wire, or the like. Introducer 18 is about 20–80 mm long, about 3–5 mm in diameter, and is tapered for insertion of access device 10, first through the upper GI tract, and then, as shown in FIG. 2, through gastric opening 8, and abdominal opening 4. The distal portion of sheath 12 contains longitudinal folds and introducer 18, which is hollow and covers the distal end of sheath 12. Locator 14 attaches to the inside of sheath 12 approximately 5–10 cm from the distal end of access device 10. The outer diameter of locator 14 is approximately 20–25 mm, and the inner diameter is approximately 15–18 mm. Locator 14 is toroidally shaped and is preferably made from a soft, flexible material such as silicone rubber, but may be made from any one of a number of biocompatible plastics and elastomers.

Dilator 16 can be a balloon having an inflated diameter of approximately 20 mm and a length of approximately 10 cm. An operator may inflate dilator 16 by injecting a fluid such as saline through fitting 26 that is external to the patient and fluidly communicates with dilator 16 via dilation tube 22. Dilator 16 may be made from a polymer such as PET, PVC, or polyurethane. (In an alternate embodiment not shown, dilator 16 may comprise a remotely expandable scaffold of rigid elements.) Sheath 12 retains dilator 16 so that a portion of dilator 16 is substantially distal to locator 14. Dilator 16 attaches to the inner surface of sheath 12 with a biocompatible adhesive or tape. Distal to locator 14 is a sheath port 24 (see FIG. 5) to allow endoscopic instruments to extend out of the distal end of access device 10 and into abdominal cavity 3. Prior to actuation of dilator 16 to an expanded configuration, sheath port 24 can be held closed by tape or other adhesive means between the folds of sheath 12. When an operator actuates (inflates) dilator 16 to change from a small configuration to the expanded configuration (by injection of saline, for example), the longitudinal folds of sheath 12 separate to open sheath port 24. Lumen 13 of access device 10, therefore, is substantially sealed from the contents of the stomach and upper GI until the operator is confident that sheath port 24 is properly positioned in abdominal cavity 3. The operator then may actuate dilator 16 to open sheath port 24. In another embodiment not shown, sheath port 24 may be covered with a thin membrane that is easily penetrated by the flexible endoscope or another endoscopic instrument.

In yet another embodiment not shown, sheath 12 initially has no sheath port, and the distal end of sheath 12 is closed. The operator pulls (or otherwise positions) distal end of sheath 12 through abdominal opening 4 and then cuts a port into the distal end of sheath 12. The operator may then gently push the distal end of sheath 12 back into abdominal cavity 3.

In yet another embodiment (not illustrated) the sheath port 24 can comprise a slit in the distal end of sheath 12 which is surrounded by elastically contractible material which maintains the port 24 in a generally closed configuration until a flexible endoscope is guided through the slit to open port 24.

A physician may use access device 10 according to the following method of the present invention in order to create an aseptic pathway for endoscopic instruments through the upper GI tract and into the abdominal cavity of a patient. The physician initially positions a guide wire into the upper GI tract. As noted earlier, there are numerous standardized methods for placing a guide wire into the upper gastrointestinal track (for subsequential placement of a PEG tube) so that a first end of the wire extends out the mouth of the patient, and a second end of the guide wire extends out of the gastric and abdominal walls. In one example of such a method, the physician first performs a standard upper endoscopy to exclude the presence of significant peptic ulceration, gastric outlet obstruction, and tumor. The physicians selects a site for guide wire introduction at the site of maximal transillumination of the abdominal wall by the light of the endoscope or by endoscopically viewing external finger tip palpation of the abdomen. The physician cleans the site selected, applies a local anesthetic, and makes a small 3–5 mm incision. Then the physician thrusts a large gauge needle catheter through the incision in the abdominal wall and into the stomach, removes the stylet within the catheter, and passes a loop of guide wire into the stomach. The physician then uses a polypectomy snare, biopsy forceps, or an equivalent device inserted through the working channel of the endoscope, to close around the first end of the guide wire, and pulls it through the upper GI and out of the patient's mouth, while being sure that the second end of the guide wire remains external to the abdomen.

The physician next releasibly attaches tether 20 of access device 10 of FIG. 1 to the first end of the guide wire, using any one of numerous methods, including tying, taping, hooking, and the like. The physician then pulls the second end of the guide wire to pull the distal portion of access device 10 into the mouth, through the esophagus, and into the stomach. As shown in FIG. 2, tether 20 passes through gastric opening 8 of gastric wall 6 and abdominal opening 4 of abdominal wall 2.

Figure 3:
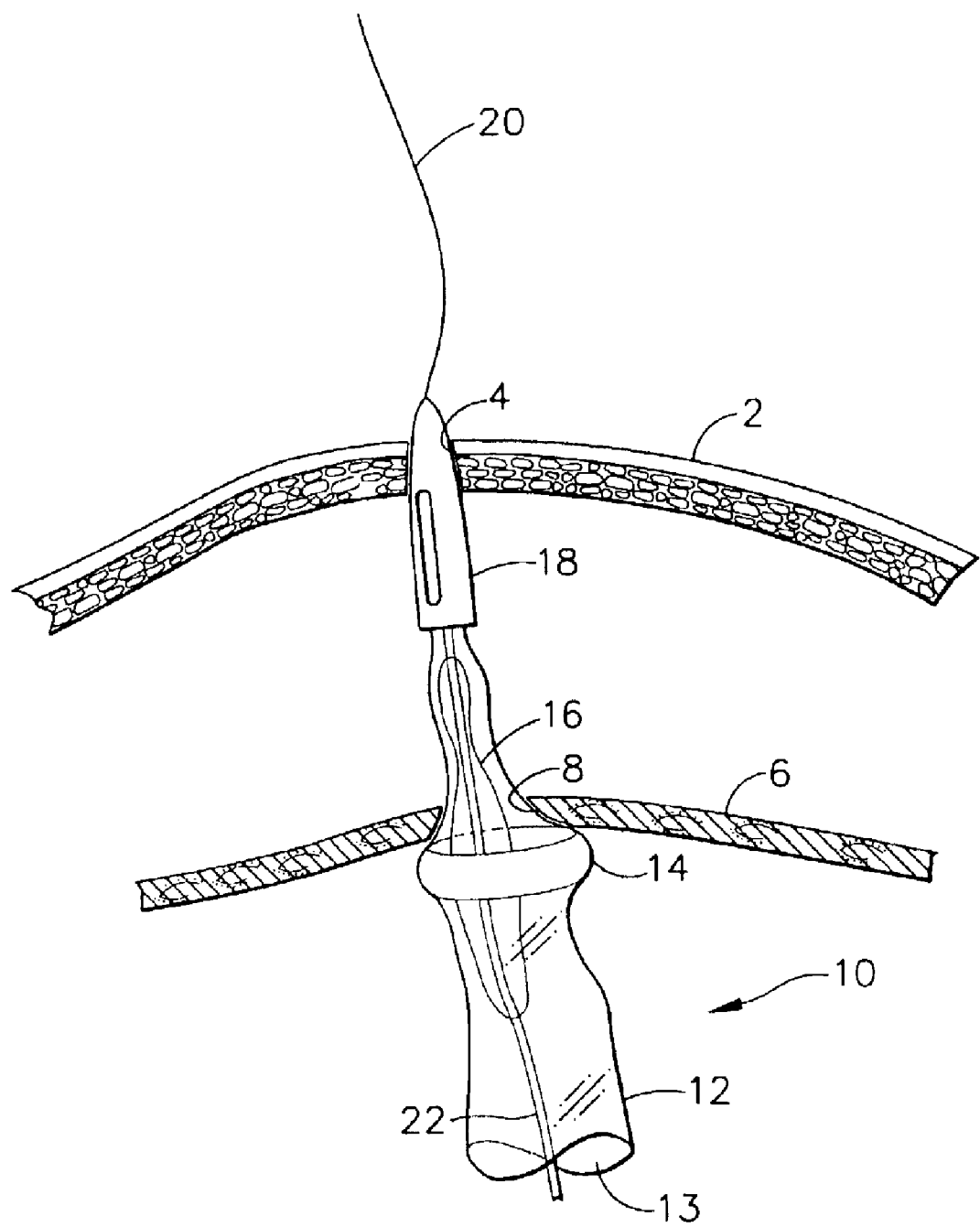
FIG. 3 illustrates the distal portion of access device 10 positioned in gastric wall 6 and abdominal wall 2.

The physician continues to gently pull tether 20 extending from abdominal opening 4 so that introducer tip 18 of access device 10 passes through gastric opening 8 and abdominal opening 4, as shown in FIG. 3. Locator 14 abuts the inside of gastric wall 6 and the physician feels a resistance on tether 20 to indicate proper positioning of access device 10 within the stomach.

Figure 4:
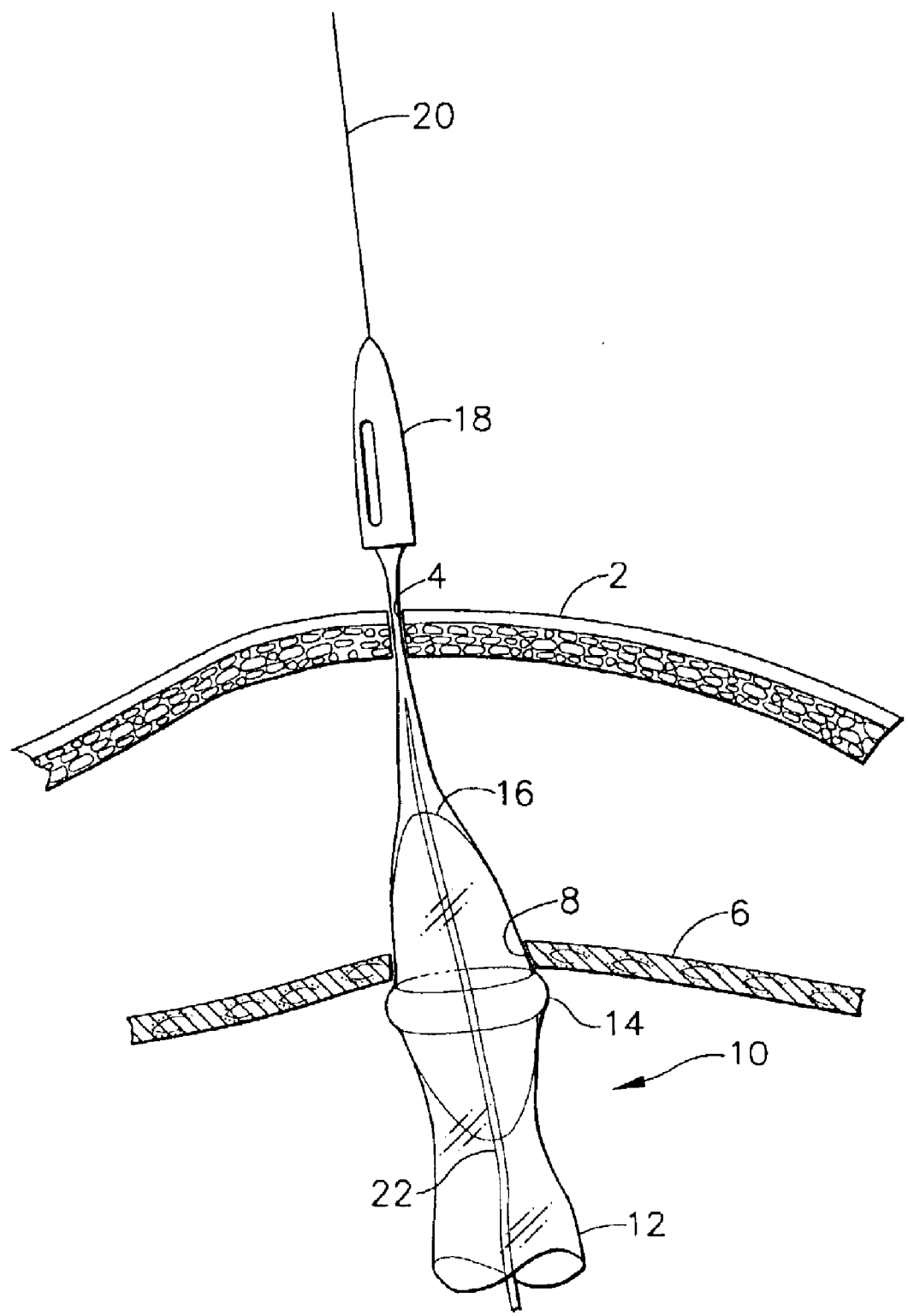
FIG. 4 illustrates a dilator 16 of access device 10, wherein dilator 16 has been actuated in order to increase the size of gastric opening 8.
Figure 5:
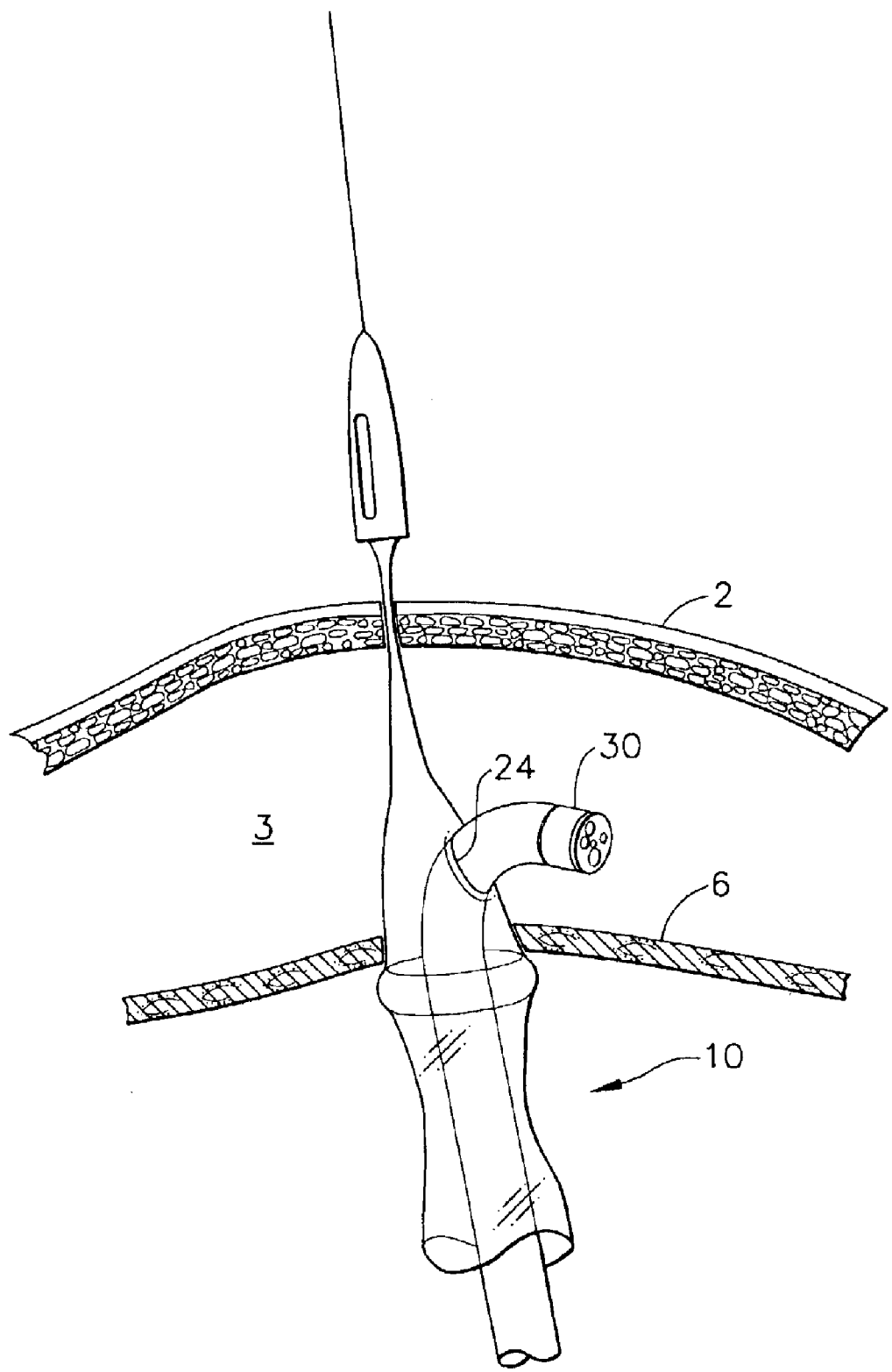
FIG. 5 illustrates access device 10 with dilator 16 removed and with an endoscope 30 introduced through access device 10 and into abdominal cavity 3 of the patient.

The physician next inflates dilator 16 by injecting a fluid such as saline into fitting 26 (see FIG. 1), thus dilating gastric opening 8 to a predetermined diameter, which is in the range of approximately 15–25 mm, as shown in FIG. 4. As dilator 16 expands, the distal portion of sheath 12 surrounding dilator 16 unfurls, opening port 24 for passage of endoscopic instruments into the abdominal cavity, as shown in FIG. 5. The physician deflates dilator 16 and pulls dilator tube 22 and dilator 16 out of the proximal end of lumen 13 of access device 10. Access device 10 fits tightly in gastric wall 6, thus impeding passage of gastric fluids into the abdominal cavity. The physician may remove introducer tip 18 by sliding it off of tether 20. By maintaining tension on tether 20, the physician keeps locator 14 positioned against the interior of gastric wall 6 to help maintain a seal at the gastrostomy and stabilize the stomach during the medical procedure. The physician may clamp tether 20 to a sterile surgical drape over the patient's abdomen in order to maintain the desired tension on tether 20 without manual holding. By adjusting the tension of tether 20 during the procedure as required, the physician has some control of the mobility of the stomach, allowing reorientation of the distal portion of access device 10 within abdominal cavity 3. The physician may next insert endoscope 30 and other endoscopic instruments (not shown) to the tissue site of interest within abdominal cavity 3 and may perform the medical procedure.

Figure 6:
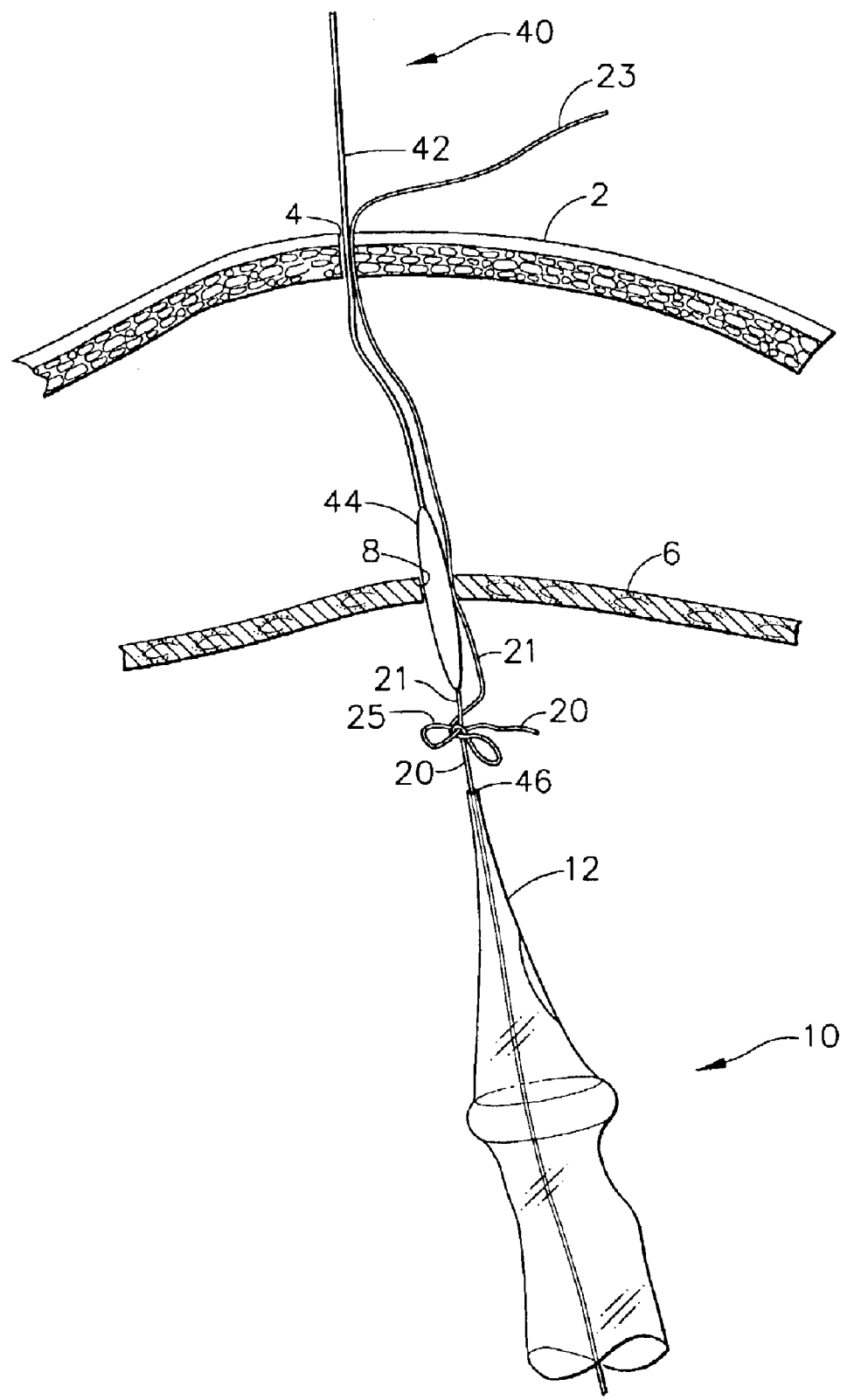
FIG. 6 illustrates a fixation device 40 attached to access device 10 and positioned in abdominal wall 2 and gastric wall 6.

When the physician has completed the medical procedure inside abdominal cavity 3, the physician removes endoscope 30 and the other endoscopic instruments from the patient. The physician then attaches a fixation device 40 to tether 20. As shown in FIG. 6, one exemplary embodiment of fixation device 40 comprises a retention balloon 44 connected to a tube 42 and a tie 21. The physician releasably joins device 10 and device 40, such as by making a bowknot 25 using tether 20 of access device 10 and tie 21 of fixation device 40, and then pulls on the proximal end of access device 10, thus removing access device 10 from gastric wall 6 and simultaneously inserting balloon 44 into the stomach. A free end 23 of tie 21 trails from bowknot 25 and extends loosely from abdominal opening 4. The physician may pull on free end 23 to untie bowknot 25, thus disconnecting fixation device 40 from access device 10, so that access device 10 may be completely removed from the mouth of the patient.

Figure 7:
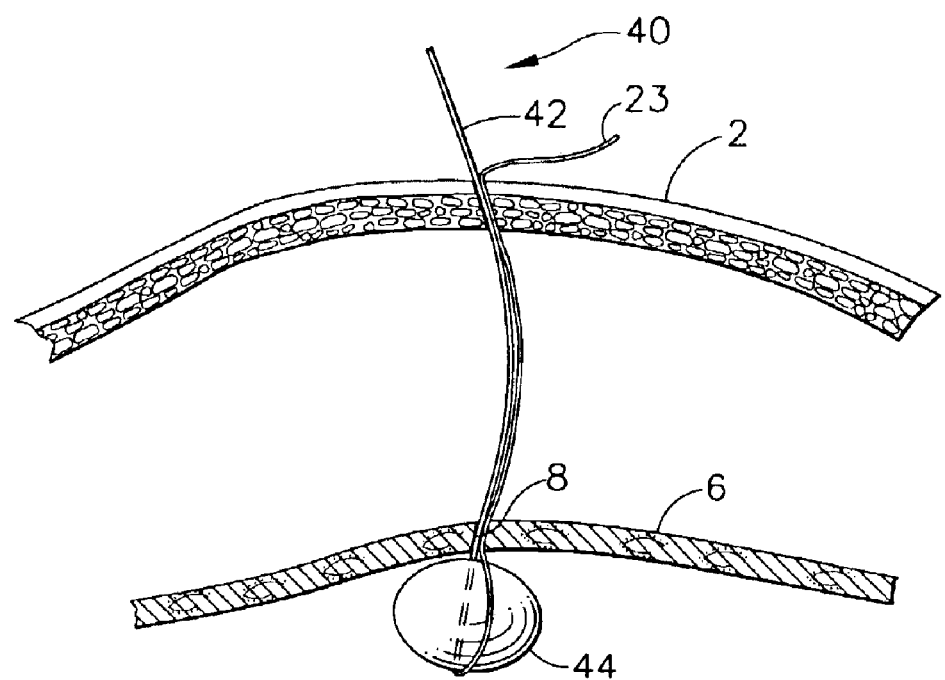
FIG. 7 illustrates a retention balloon 44 of fixation device 40, wherein support element 44 is actuated to support gastric wall 6.
Figure 8:
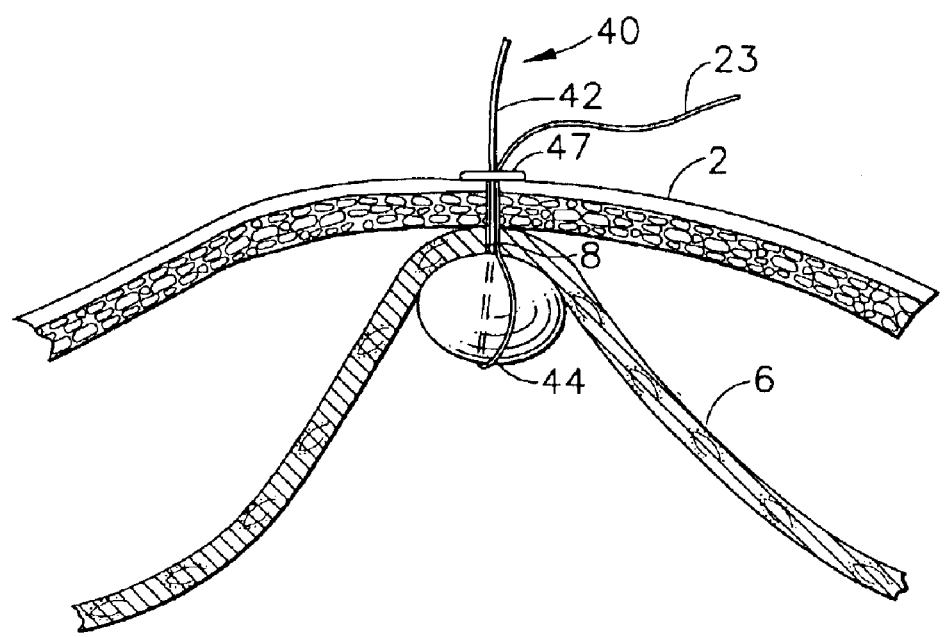
FIG. 8 illustrates fixation device 40 holding gastric wall 6 and abdominal wall 2 together.

FIG. 7 illustrates balloon 44 of fixation device 40, after the physician has expanded balloon 44 by injecting a fluid such as saline into fixation tube 42. The physician then may gently pull tube 42 upwards to bring gastric wall 6 and abdominal wall 2 into contact. The physician places a retention element 47 onto tube 42 to maintain fluid pressure inside balloon 44 and to hold gastric wall 6 and abdominal wall 2 together during healing, as shown in FIG. 8. Free end 23 of tie 21 may be trimmed away or left trailing out of abdominal opening 4.

In a few days, when gastric wall 6 has healed to abdominal wall 2, and gastric opening 8 is physiologically sealed from abdominal cavity s, the physician removes retention element 46, deflating balloon 44, so that fixation device 40 may be pulled out of the patient. The wound may then be cleaned and dressed using conventional procedures developed for treatment of wounds after PEG tube placement and removal.

Figure 9:
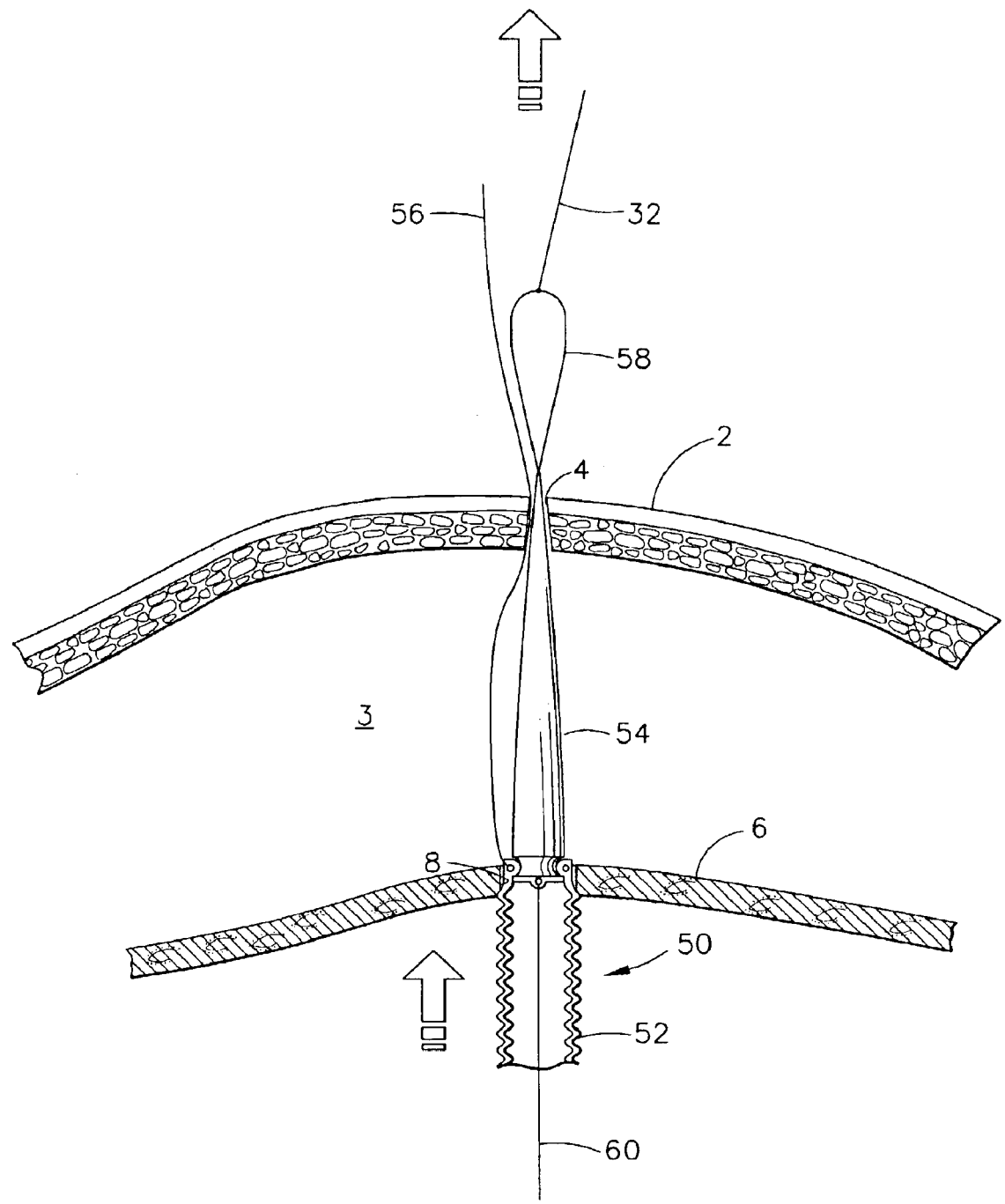
FIG. 9 illustrates the distal portion of a second embodiment of the present invention, an access device 50, initially positioned in gastric opening 8.
Figure 10:
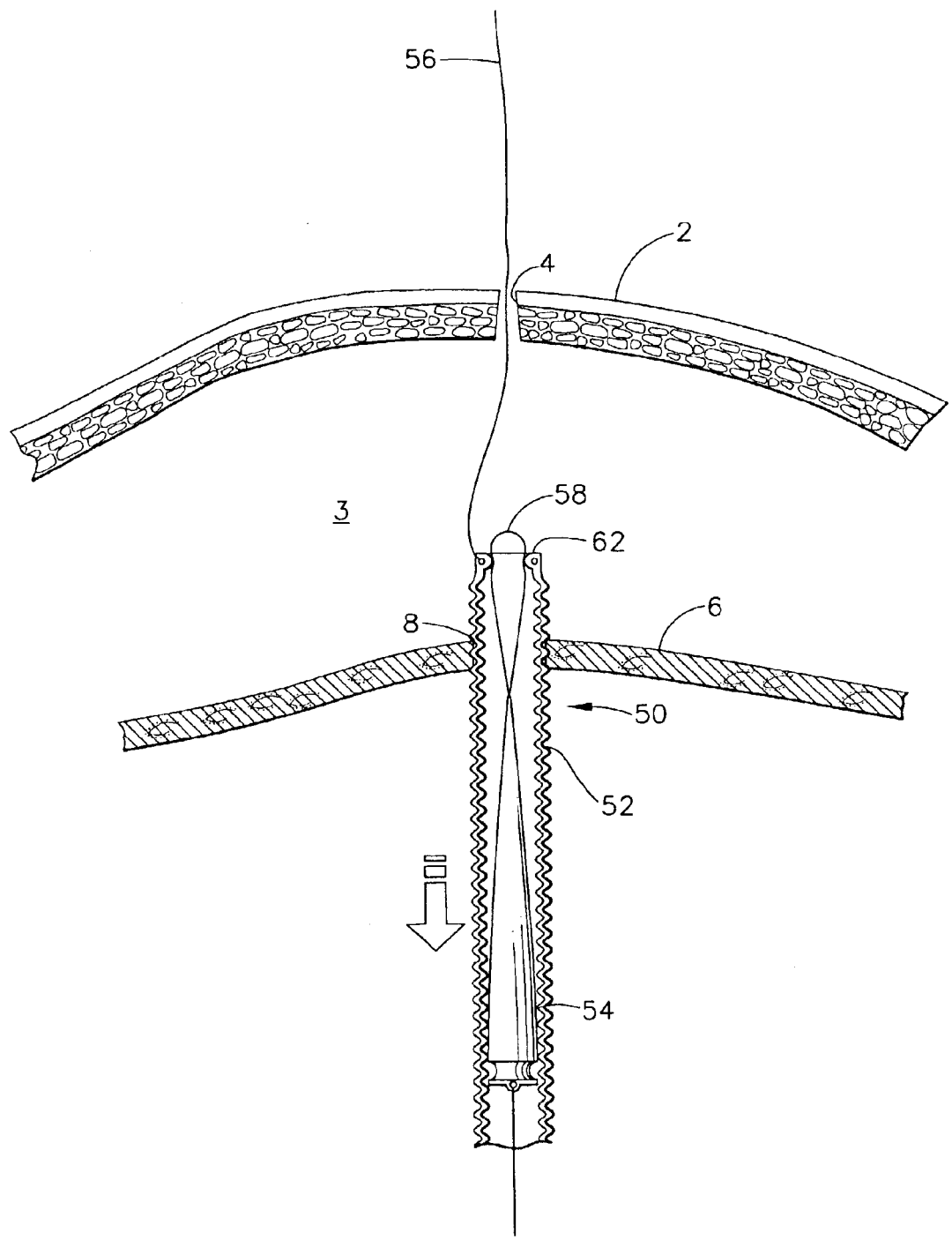
FIG. 10 illustrates access device 50 retained in gastric opening 8 by a tether 56 while an operator pulls on a cord 60 to remove a dilator 54 from the patient.
Figure 11:
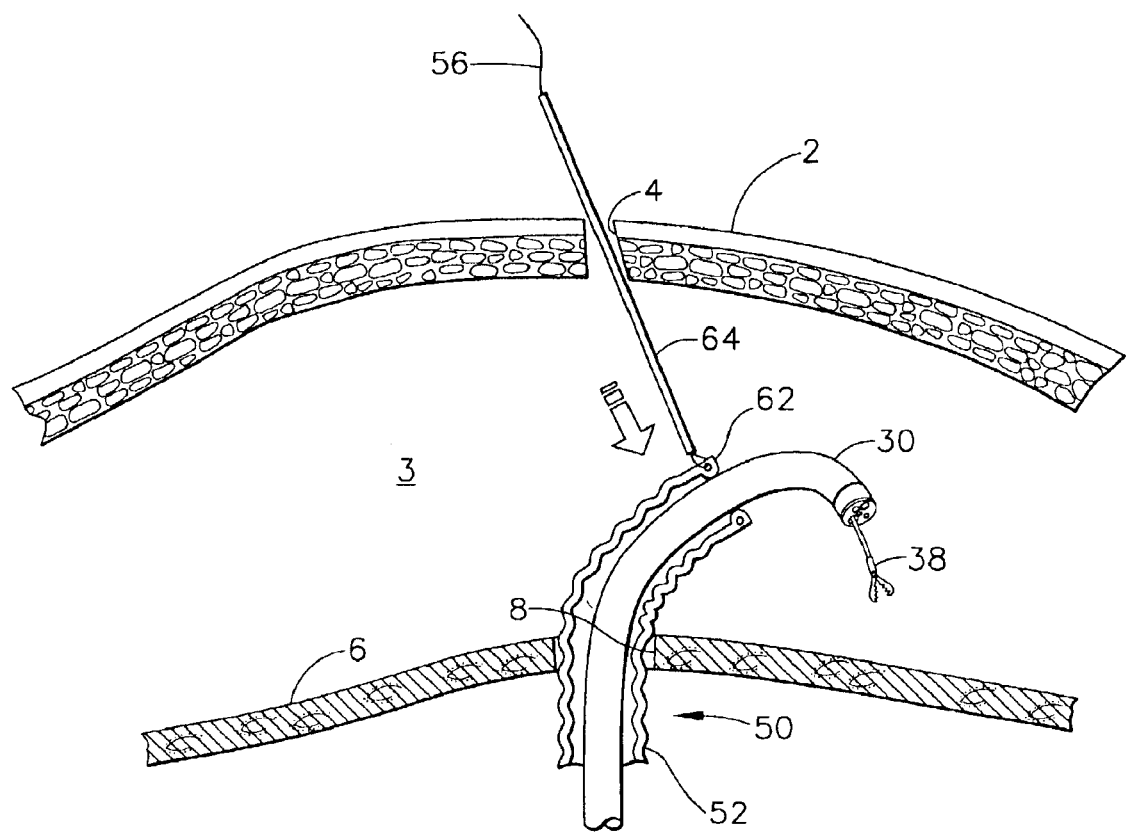
FIG. 11 illustrates a steering element 64 slidably positioned over tether 56 for manipulating distal end 62 of access device 50 within abdominal cavity 3, thereby directing endoscope 30 to the desired tissue site.

FIGS. 9, 10, and 11 illustrate a second embodiment of the method of the present invention, which includes providing an access device 50 comprising a detachable, dilator 54 removably attached to a convoluted tube 52. Dilation tip 54 is preferably made of an elastomer such as silicone rubber and is shaped approximately the same as a bougie dilator in this embodiment, although other shapes are possible. A pull loop 58 connects to the distal end of dilation tip 54, and attaches to a guide wire 32 for placement into the upper GI tract. A cord 60 attaches to the proximal end of dilation tip 54 and extends through convoluted tube 52 and out of the proximal end of convoluted tube 52. Convoluted tube 52 is made of a biocompatible, extruded polymer such as polyethylene. Convoluted tube 52 resists kinking, thereby maintaining an open lumen and facilitating flexible endoscopic instrument exchange. FIG. 9 shows access device 50 after a physician has used guide wire 32 in a similar manner as described for the previous embodiment to placed access device 50 into the upper GI so that loop 58 extends out of abdominal opening 4. The distal end 62 of convoluted tube 52 retains dilation tip 54 only when loop 58 is pulled in the distal direction. The physician then may detach guide wire 32 from loop 58. The physician then may detach dilation tip 54 from distal end 62 of convoluted tube by pulling cord 60 in the proximal direction while simultaneously pulling a tether 56 attached to convoluted tubing 52 and extending out of abdominal opening 4. As shown in FIG. 10, the physician may remove dilation tip 54 by continuing to pull cord 60 extending out of the proximal end of convoluted tube 52. Dilator 52 can be made of a flexible, compressible material and can be hollow, so that dilator 52 collapses or otherwise deforms as it is pulled proximally through the lumen of convoluted tube 52.

FIG. 11 shows convoluted tube 52 extending through gastric opening 8 and into abdominal cavity 3, and containing an endoscope 30 and an instrument 38. A physician may place a steering element 64 over tether 56 as shown in FIG. 11 and manipulate (much like a "joystick") the position of distal end 62 of access device 50 within abdominal cavity 3. Steering element 64 may be made of a rigid metal or plastic tube having an outside diameter approximately in the range of 2–5 mm, and a length approximately in the range of 15–25 cm. Steering element 64 may be straight, as shown in FIG. 11, curvilinear, or combinations thereof. Alternately, steering element 64 may be plastically deformable so that a user may alter its shape prior to or even after insertion into the patient.

Steering element 64 can be hollow, and can be sealed, such as at one or both ends, such as with a seal of the form shown with respect to seal 11 that can provide sealing around an instrument inserted through the hollow element 64. In one embodiment, steering element 64 can be in the form of a trocar cannula for use inserting one or more medical instruments, therethrough.

If the steering element is hollow, the central bore of the steering element 64 can be in fluid communication (such as by a flexible hose) to a source of liquid or gas, such as, but not limited to, a source of vacuum or a source of saline. For instance, steering element 64 may also be adapted to include means for suction, irrigation, illumination, visualization, insufflation (with CO2, for example), drug delivery, and other surgical functions. Steering element 64 may be attached to an external support member (not shown) attached, for example, to the examination table, for holding distal end 62 at a desired position within abdominal cavity 3 for a period of time.

Steering element 64 can be releasably attached to one or more other devices in the body cavity, and may include other attachment means including without limitation hooks and graspers. Tile length of the steering element 64 can be selected for a particular application, or alternatively the length can be variable, such as by incorporating a "telescoping" function in the steering element 64. The steering element can be adapted to be relatively rigid, relatively flexible, include articulation (e.g. such as one or more hinge joints), and combinations thereof.

Various embodiments of the present invention have been illustrated, but it will be obvious to those skilled in the art that such embodiments are only examples and that numerous variations and substitutions are possible without departing from the invention. For instance, while the invention has been illustrated with respect to use in accessing the abdominal cavity, the invention can also be used for accessing other body cavities, including without limitation the thoracic cavity. It is intended that the invention be limited only by the scope and spirit of the appended claims.

What is claimed:

1. A method for accessing a body cavity, the method comprising:

introducing a medical device into the body cavity;

providing a percutaneous incision to access the body cavity;

steering the medical device through the percutaneous incision;

wherein the step of steering comprises extending a steering element through the percutaneous incision to manipulate a portion of the medical device.

2. The method of claim 1 wherein the step of introducing comprises introducing the medical device through a naturally occurring body orifice.

3. The method of claim 1 wherein the step of introducing a medical device comprises introducing a flexible endoscope.

4. The method of claim 1 wherein the step of introducing the medical device comprises introducing the medical device into the upper gastrointestinal tract and through a gastric opening into the abdominal cavity.

5. The method of claim 1 wherein the step of steering the medical device comprises steering the distal end of an endoscope positioned in the abdominal cavity.

6. The method of claim 1 wherein the steering element is hollow.

7. The method of claim 6 communicating a vacuum source with said hollow steering element.

8. The method of claim 6 comprising extending a tether through said hollow steering element.

9. A method for accessing a body cavity, the method comprising:

introducing a medical device transorally into the gastrointestinal tract;

providing an opening communicating from inside the gastrointestinal tract to the body cavity;

directing a portion of the medical device into the body cavity through the opening communicating from inside the gastrointestinal tract to the body cavity;

providing an incision communicating from outside the body to the body cavity; and manipulating a portion of the medical device disposed in the body cavity through the incision.

10. The method of claim 9 wherein the step of providing an opening communicating from inside the gastrointestinal tract to the body cavity comprises providing an opening in the wall of the stomach.

11. The method of claim 10 further comprising providing a seal at the opening in the wall of the stomach.

12. The method of claim 9 wherein the step of steering comprises extending a steering element through the incision to manipulate a portion of the medical instrument.

13. The method of claim 9 wherein the step of providing the incision communicating from outside the body cavity comprises forming the incision from outside the body.

14. A method for accessing a body cavity, the method comprising:

providing an opening through the wall of the stomach into the abdominal cavity;

providing an incision through the abdominal wall into the abdominal cavity;

introducing a medical device transorally into the stomach;

directing a distal portion of the medical device through the opening in the wall of the stomach to be disposed In the abdominal cavity; and manipulating tho distal portion of the medical device disposed in the abdominal cavity through the incision through the abdominal wall.

* * * * *